United States Patent [19]

Scwemberger et al.

[11] Patent Number: 5,569,292
[45] Date of Patent: Oct. 29, 1996

[54] SURGICAL PENETRATION INSTRUMENT WITH TRANSPARENT BLADES AND TIP COVER

[75] Inventors: Richard F. Scwemberger, Cincinatti; Salvatore Privitera, West Chester; Robert Hughes, Cincinatti, all of Ohio

[73] Assignee: Ethicon Endo-Surgery, Inc., Cincinatti, Ohio

[21] Appl. No.: 382,462

[22] Filed: Feb. 1, 1995

[51] Int. Cl.$^6$ ................................................ A61B 17/34
[52] U.S. Cl. .......................... 606/185; 606/167; 604/264; 600/101
[58] Field of Search ................................ 606/1, 167, 170, 606/171, 184, 1 A; 604/164, 264, 172, 272; 600/101

[56] References Cited

U.S. PATENT DOCUMENTS

| | | |
|---|---|---|
| 4,535,773 | 8/1985 | Yoon . |
| 5,226,426 | 7/1993 | Yoon . |
| 5,271,380 | 12/1993 | Riek et al. . |
| 5,304,193 | 4/1994 | Zhadanov ............................ 606/185 |
| 5,334,150 | 8/1994 | Kaali . |
| 5,376,076 | 12/1994 | Kaali ................................... 606/185 |
| 5,385,572 | 1/1995 | Nobles et al. ...................... 606/185 |
| 5,441,041 | 8/1995 | Sauer et al. ........................ 606/185 |

OTHER PUBLICATIONS

United States Surgical Corporation, VISIPORT* Disposable Optical Trocar Insert, Norwalk, Connecticut, 1994.

*Primary Examiner*—Glenn Dawson
*Attorney, Agent, or Firm*—Matthew S. Goodwin

[57] ABSTRACT

A surgical penetration instrument has an elongated shaft and a penetrating tip extending from the distal end of the shaft. A blade extends outwardly from the penetrating tip. The blade is transparent. When the penetrating tip is transparent, the tip not only facilitates penetration through bodily tissue but also acts as an imaging element in conjunction with an endoscope extending through the shaft of the instrument to simultaneously visualize the surgical field during penetration. Significantly, unlike a conventional metallic blade, the transparent blade will not obstruct the field of view as the instrument is advanced. When the penetrating tip is plastic, and the blade is composed of a transparent plastic, the blade can be joined to the tip using conventional plastic processing methods such as injection molding, thus reducing manufacturing costs incurred if a metallic blade were used. Also disclosed is a surgical penetration instrument with a plastic penetrating tip and a protective cap fitting over and enclosing a portion of the tip to prevent or lessen the possibility of breaking, cracking or otherwise damaging the tip.

24 Claims, 6 Drawing Sheets

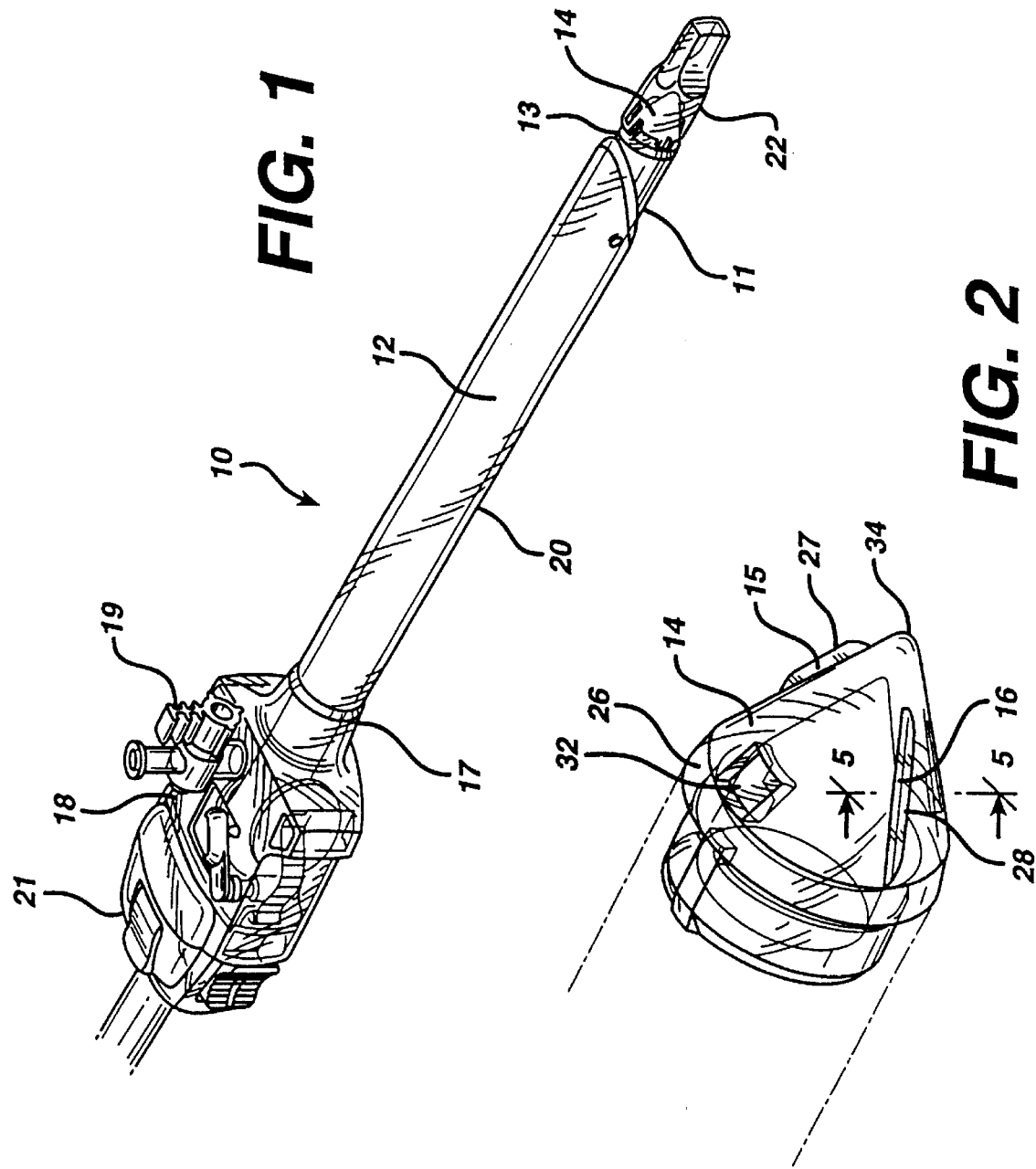

SURGICAL PENETRATION INSTRUMENT WITH TRANSPARENT BLADES AND TIP COVER

BACKGROUND OF THE INVENTION

This invention relates to a surgical instrument for penetrating bodily tissue during a surgical procedure. More particularly, it relates to surgical penetrating instruments which have an elongated shaft and a penetrating tip extending from the shaft. These penetrating instruments may not only allow for penetration into tissue as the instrument is advanced, but also simultaneously provide for the ability to visualize the penetrated tissue during the advancement.

One of the key surgical activities which is required during every surgical procedure is the creation of an access opening into the body cavity at the desired surgical site. For many years, the surgeon created the access opening by simply making a large incision through the body wall to expose the body cavity. The length of the incision would depend on the size of conventional surgical instruments and the ability of the surgeon to properly and efficiently use these instruments within the body cavity through the incision created. Once the surgeon finished the surgical procedure, the incision could be fastened using known techniques. Unfortunately, due to the nature of these conventional, open surgical procedures, long incisions were often necessary. Open surgery can therefore be traumatic to the patient because, among other things, the recuperative period required to fully heal from the effects of the large incision may be significant.

Since a patient's recuperative period can be significant in connection with conventional open surgery, new surgical procedures and instruments to support those procedures are becoming available. The most popular alternative to open surgery currently is endoscopic surgery. Endoscopic surgery involves the use of a number of small diameter openings providing access into the body cavity. Unlike the large incisions required for open surgery, these small diameter openings readily heal following surgery, and require much less recuperation time for the patient.

The cornerstones which have made endoscopic surgical procedures possible are the miniaturized camera, or endoscope, and the surgical penetration instrument providing the small diameter opening for access into the body cavity, conventionally referred to as the trocar. Since both of these instruments are critical for the performance of endoscopic surgery, each will be discussed briefly below.

An endoscope is an elongated, generally cylindrical imaging and visualization instrument. It can be attached to a light source which provides illumination within the body cavity at the surgical site. The endoscope contains a miniaturized camera lens which is capable of transmitting the illuminated images at the surgical site to the surgeon during a surgical procedure. The endoscope is frequently attached to a video monitor during endoscopic surgery, so that the surgical team can observe the surgical procedure within the body cavity on the video monitor screen. The endoscope has made it possible to indirectly observe the surgical procedure without having the direct access into the body cavity, and consequently the large incisions it requires to create such direct access.

Critical to the success of endoscopic surgery is the creation of a small diameter passageway into the body cavity for subsequent insertion and withdrawal of surgical instruments. These instruments include, for example, an endoscope, and elongated instruments to cut, fasten, coagulate and excise desired tissue. The trocar has become the instrument of choice to create this small diameter passageway. A trocar is a penetrating assembly including a cutting tool, commonly referred to as the trocar obturator. The obturator has an elongated, cylindrical shaft from which extends a penetrating tip to create and enlarge an opening into tissue as the obturator is advanced. The obturator is slidably received in a sleeve, commonly referred to as the trocar cannula. As the obturator is advanced into the tissue, the cannula likewise is advanced. When the obturator has completely punctured the body wall, the obturator is withdrawn from the trocar assembly, leaving behind the trocar cannula. The trocar cannula then provides the passageway into the body cavity through a relatively small diameter opening.

One of the first technical challenges in connection with the design and manufacture of the trocar related to the incorporation of features into the trocar to enhance its safety. Specifically, it was important to develop a safety trocar which could substantially lessen the possibility of unintentional tissue or organ puncture. The seminal patent that describes a mechanism for protecting bodily tissue and organs from inadvertent puncture during advancement of the instrument into the body cavity is U.S. Pat. No. 4,535,773 (Yoon, issued August, 1985). This patent describes a trocar assembly which includes a safety shield interposed between the trocar obturator and cannula. The shield is biased in an extended position to cover the penetrating tip of the obturator. When the surgeon desires to penetrate tissue with the trocar, the safety shield retracts and exposes the penetrating tip when the surgeon applies pressure against the body wall. The shield remains in the retracted position so long as pressure is continuously applied. When the surgeon fully punctures the body wall, the pressure is relieved and the safety shield returns to its extended position covering the penetrating tip. Therefore, inadvertent puncture of bodily tissue and organs within the body cavity can be avoided. Another trocar assembly with a safety shield mechanism is described in U.S. Pat. No. 5,226,426 (Yoon, issued July 13, 1993). This patent describes a trocar obturator in the form of a hollow needle through which the safety shield (or safety "probe"), is disposed. Once again, the safety probe covers the sharp tip of the needle until pressure is applied during insertion.

Since the development of the safety-shielded trocar, other mechanisms for protecting tissues and organs from inadvertent puncture during endoscopic surgery have been developed. For example, mechanisms have been developed where the obturator retracts into the trocar cannula after puncture. These "retractable obturator" trocars may be equipped with a safety shield which simultaneously moves to an extended position as the obturator retracts within the trocar cannula.

While numerous trocar assemblies have been designed to prevent inadvertent puncture, all of these instruments still have one basic problem. Regardless of the safety mechanisms built into these instruments, the surgeon cannot avoid the fact that he is still puncturing tissue blindly. Not only is the puncture performed blindly, but the instruments are expensive to manufacture and occasionally fail in connection with the safety features incorporated to prevent inadvertent puncture during the blind insertion. Therefore, significant new designs for trocar assemblies have been developed.

One of the more remarkable developments in the design of trocar assemblies relates to the incorporation of visualization concurrently with penetration. This has been made possible by the "marriage" of the endoscope for imaging and visualization, and the trocar for penetration to provide the endoscopic access opening. The first patent to describe a surgical penetration instrument adapted for visualization during penetration is U.S. Pat. No. 5,271,380 (Riek, et al., issued Dec. 21, 1993). The Riek patent describes a penetrating instrument including a hollow, cylindrical sleeve and an imaging element attached to the sleeve at its distal end. The imaging element is a transparent, optical "window". In a preferred embodiment, it has a conical configuration to facilitate the advance of the instrument into body tissue. A fiber optic cable extends through the hollow shaft and is positioned adjacent the proximal end of the window. It delivers light from a light source through the optical window into surrounding bodily tissue. A camera lens is also provided in the shaft to deliver illuminated images transmitted through the optical window to the surgeon. When the surgeon advances the instrument into bodily tissue, the surgeon can view the tissue in front of and surrounding the optical window during the penetration. This feature is significant because the surgeon can adjust the path of advancement if he approaches tissue or organs which should not be touched. In this way, the incorporation of a safety shield or another mechanism to protect tissue or organs from inadvertent puncture during a blind insertion is unnecessary.

Another recently issued patent representing yet another significant advance in the state of the art with respect to surgical penetration instruments providing simultaneous visualization is U.S. Pat. No. 5,334,150 (Kaali, issued Aug. 2, 1994). The Kaali patent also describes an instrument including an elongated hollow shaft to which is attached an imaging element is the preferred form of a transparent conical window. However, instead of extending a fiber optic cable and lens into fixed positions adjacent the proximal end of the transparent window within the hollow shaft, the Kaali patent describes using a fully integrated endoscope which can be inserted through the hollow shaft adjacent the window to provide illumination and visualization of tissue in front of and surrounding the transparent window during insertion.

Recently, the incorporation of a cutting blade extending outwardly from the transparent optical window of the surgical penetration instruments described in the Riek and Kaali patents has been accomplished. The purpose of the blade is to facilitate the advance of the instrument into tissue, and therefore reduce the force required to penetrate the tissue. Unfortunately, the incorporation of the blade onto the window has highlighted some of the technical difficulties involved in connection with the integration of the blade onto the window. Specifically, the blades have been conventional metal blades. The cost of manufacturing metallic blades can be prohibitive. Additionally, the transparent optical window of these penetrating instruments is typically and conveniently composed of either a plastic material or a glass. The manufacturing methods for joining a metallic blade to these windows can be extremely difficult, time-consuming and costly. Furthermore, the presence of a metallic blade extending outwardly from the window can significantly obstruct vision when observing the penetration through the endoscope.

Finally, a plastic penetrating tip in the form of a transparent optical window may need to be handled very carefully during shipping, handling and use. Unlike metallic penetrating tips, a plastic tip may be more prone to chipping or breakage. In addition, any blade extending outwardly of the penetrating tip may also need to be protected. Unfortunately, provisions have not been made to ensure the integrity of a plastic penetrating tip on surgical penetrating instruments.

In view of certain deficiencies in connection with surgical penetration instruments permitting visualization concurrently with advancement into tissue, an improved surgical penetration instrument is required. Specifically, a blade extending outwardly from the penetrating tip to facilitate the advance of the instrument through tissue is needed which can be manufactured at a reasonable cost. Additionally, when the penetrating tip is composed of either a plastic material or a glass, it would be advantageous to develop and manufacture a blade which is more compatible and easier to process with the penetrating tip then conventional metallic blades. Further, it would be ideal if such a blade could be made which did not obstruct the field of view through the tip when the instrument is advanced. It would also be desirable to provide the means necessary to protect a plastic penetrating tip on a surgical instrument during handling and use.

SUMMARY OF THE INVENTION

In one aspect of the invention, the invention is a surgical penetration instrument for penetrating bodily tissue during a surgical procedure. The instrument comprises an elongated shaft having a distal end. A penetrating tip is in communication with the shaft distal end and extends distally from it. The penetrating tip has a surface configuration shaped to enlarge an opening in the tissue as the instrument is advanced distally into the tissue. A first blade extends outwardly of the penetrating tip. The first blade has a first linear edge surface. Significantly, the blade is transparent.

Significantly, a transparent blade extending outwardly from the penetrating tip will not obstruct the visual field when observing the advance of the instrument into tissue through an endoscope. Therefore, optical clarity is substantially increased without sacrificing the ease with which the instrument can be advanced to penetrate into tissue. The availability of numerous plastics and glasses exhibiting the requisite properties for the manufacture of blades, and further exhibiting the characteristic of transparency, provides an additional, outstanding benefit.

In addition to the desirable property of transparency, the incorporation of a transparent blade onto the penetrating tip of the surgical penetration instrument may solve numerous problems inherent in the surgical penetration instruments described in connection with the conventional instruments. Today, many of these transparent materials can be processed to provide the desired surface hardness and part geometry necessary to facilitate the advance of the instrument into tissue. In addition, these materials can be machined to further refine the geometry and linear edge surface of the blade. Furthermore, the incorporation of a plastic blade onto a plastic penetrating tip, for example, is relatively straightforward and simple. Conventional plastic processing methods such as injection molding or extrusion can be used to join the blade with the penetrating tip. Similarly, the incorporation of a glass blade onto a glass tip would be relatively straightforward as well. Thus, the incompatibility between a metallic blade and a penetrating tip composed of a different material is completely avoided.

In another aspect of the invention, the invention is a surgical penetration instrument for penetrating bodily tissue during a surgical procedure. The instrument comprises a generally cylindrical, elongated shaft having a distal end and a shaft diameter. A plastic penetrating tip is in communication with the shaft distal end. The tip has a generally circular base adjacent the shaft distal end. The base has a base diameter substantially the same as the shaft diameter. The tip extends distally from the base and has an exterior surface configuration shaped to enlarge an opening in the bodily tissue as the instrument is advanced distally into the tissue. The instrument further comprises a protective cap sized to fit over and enclose at least a portion of the tip, cap receiving means on the exterior surface of the tip for securely receiving the cap, and cap attaching means on the cap for attaching the cap onto the cap receiving means.

The protective cap enclosing at least a portion of the tip protects the tip during shipping, handling and use. The possibility of chipping, cracking or otherwise damaging the plastic penetrating tip is therefore substantially reduced.

The surgical penetration instrument of this invention is ideally suited for all applications for which convention trocars are used. These applications include, but are not limited to, various forms of endoscopic surgery, including laparoscopic and thoracoscopic surgery. It is also envisioned that the surgical penetration instrument of this invention may be used for arthroscopic surgery as well. In addition to those procedures where penetration and puncture of the body wall to provide a passageway for additional endoscopic surgical instrumentation is desired, it is also anticipated that this instrument may be used in procedures not requiring complete penetration and puncture through the body wall. For example, certain procedures require a penetrating or dissecting instrument to tunnel through layers of tissue without breaking certain other layers of tissue. Emerging procedures in connection with laparoscopic hernia repair and saphenous vein harvesting for cardiovascular surgery incorporate tunneling techniques to provide access to a desired surgical site remote from the point of entry. The surgical user may well find the surgical penetration instrument of this invention, which offers the dual capabilities of penetration and visualization, to be particularly well suited for these emerging procedures. Finally, the reader must also realize that although this instrument is particularly adapted for endoscopic surgical applications, it may also find use for a wealth of applications in conventional open surgery.

BRIEF DESCRIPTION OF THE DRAWINGS:

FIG. 1 is a perspective view of an assembly including the surgical penetration instrument of the present invention, FIG. 2 is an enlarged perspective view of the penetrating tip of the instrument.

DETAILED DESCRIPTION OF THE PREFERRED EMBODIMENT

Figure 3:
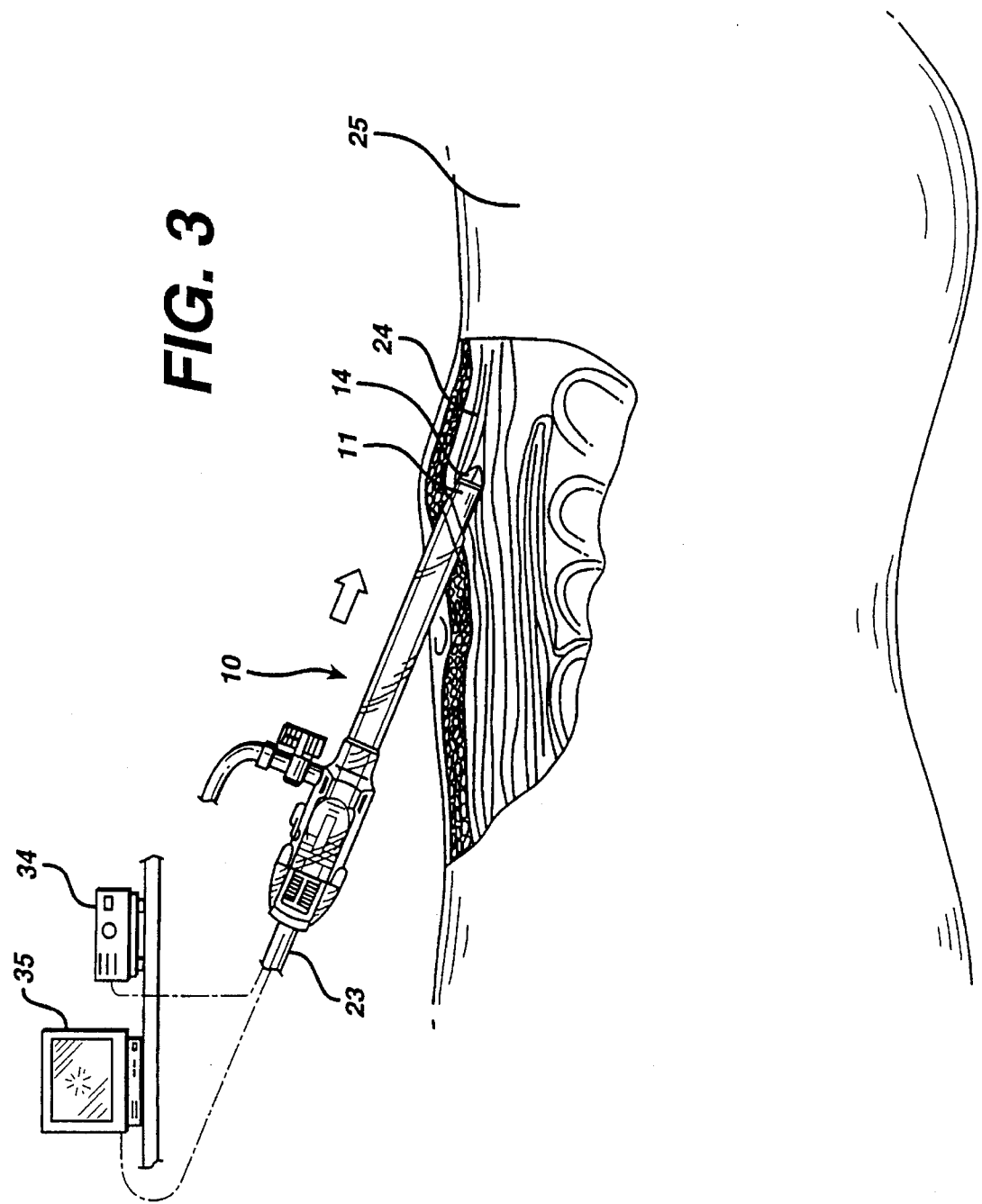
FIG. 3 is a side elevational view in partial cross-section of the assembly including the instrument shown in the process of penetrating bodily tissue in a surgical patient.

Reference numerals are used in this description to designate the various components and elements of the surgical penetration instrument of this invention. Identical reference numerals designated in the various drawings refer to the identical element or component of the surgical penetration instrument. As used in this description, "proximal" or "proximally" refers to that portion of the instrument, component or element which extends toward the user. Conversely, "distal" or "distally" refers to that portion of the instrument, component or element which extends away from the user.

Figure 4:
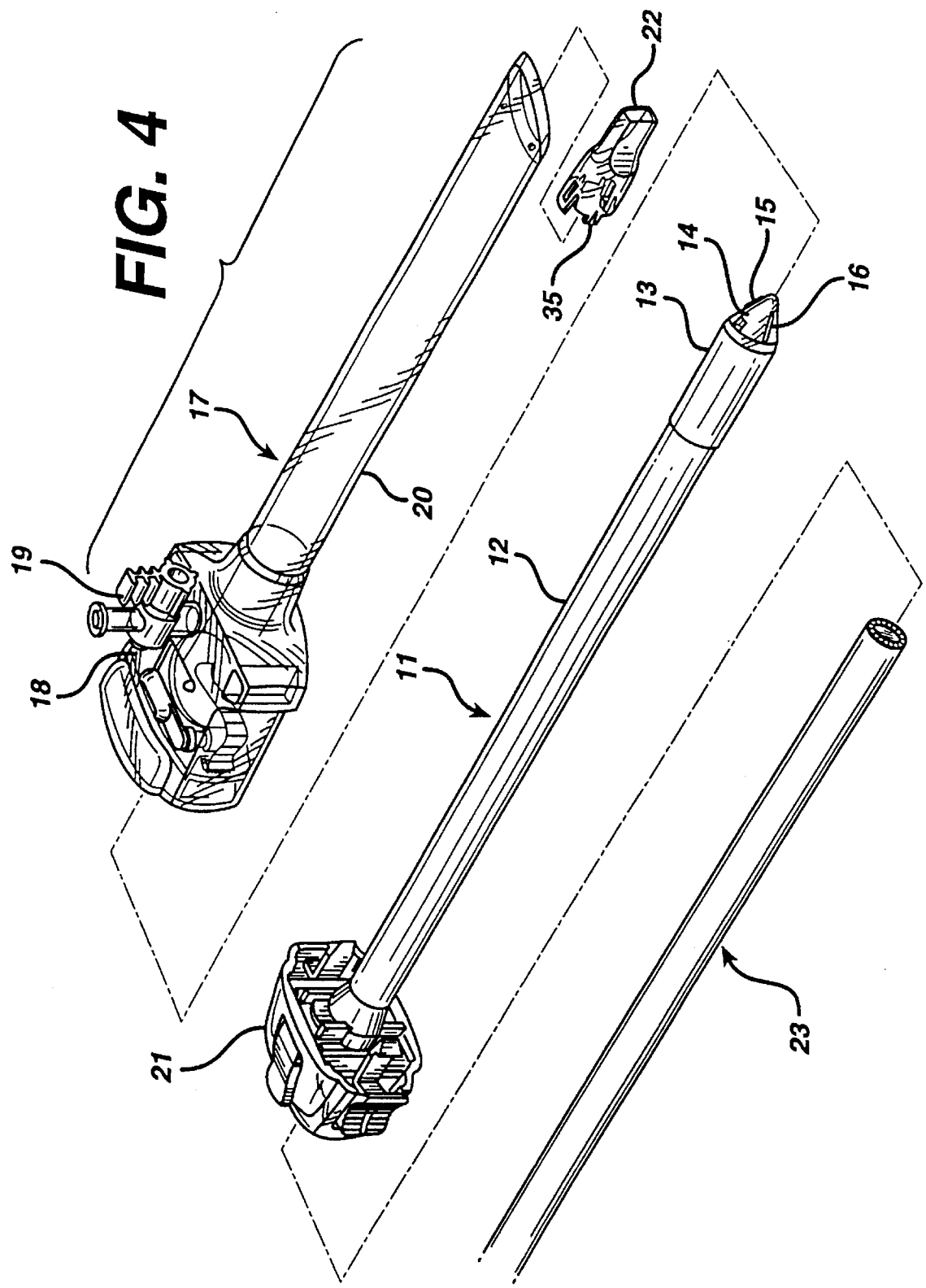
FIG. 4 is an exploded perspective view of the assembly including the surgical penetration instrument.

Referring now to FIGS. 1, 2 and 4, there is shown an assembly 10 which incorporates the surgical penetration instrument of this invention. The surgical penetration instrument 11 has a cylindrical, elongated hollow shaft 12. The shaft has a distal end 13 from which extends a conical transparent penetrating tip 14. Facilitating the penetration of tip 14 as instrument 11 is advanced into tissue are first and second blades 15 and 16, respectively, extending integrally from the transparent conical tip.

The assembly includes a conventional cannula 17. The cannula has a cannula housing 18 and stopcock 19. Extending distally from the cannula housing 18 is the cannula sleeve 20. The surgical penetration instrument 11 is inserted into and through the cannula housing 18 and sleeve 20. The transparent penetrating tip 14 of the instrument, and a portion of the shaft distal end 13 of the instrument, extend distally from the cannula sleeve 20.

The surgical penetration instrument 11 has at its proximal end an instrument hub 21. The hub can be attached to the cannula housing 18 when the instrument is inserted into and through the cannula housing and sleeve. If desired, a pressurizing fluid such as carbon dioxide can be selectively pumped through the cannula sleeve 20 via stopcock 19 into the body of the patient.

Figure 8:
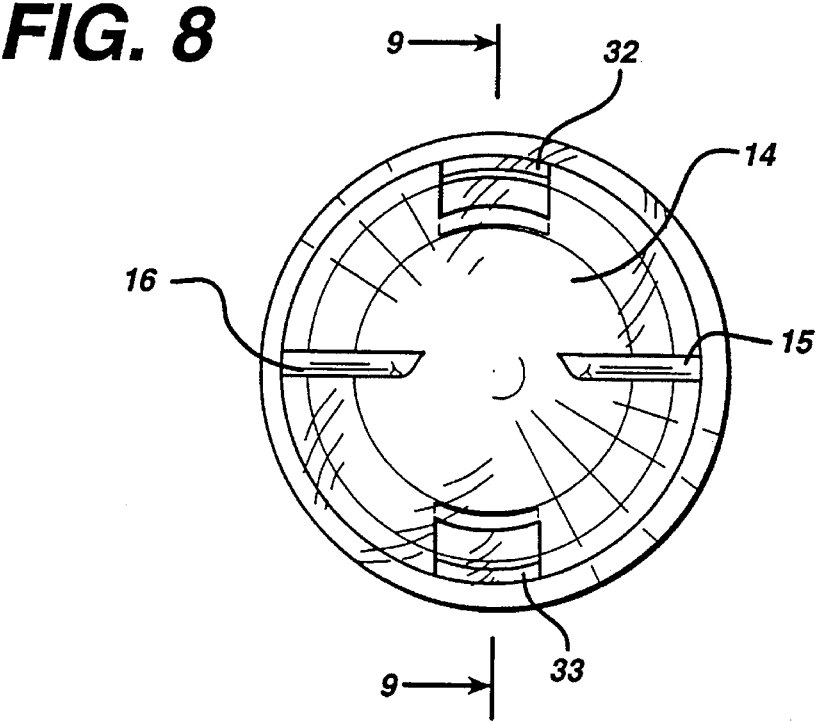
FIG. 8 is an end elevational view of the distal end of the penetrating tip as seen along view line 8—8 of FIG. 7.
Figure 9:
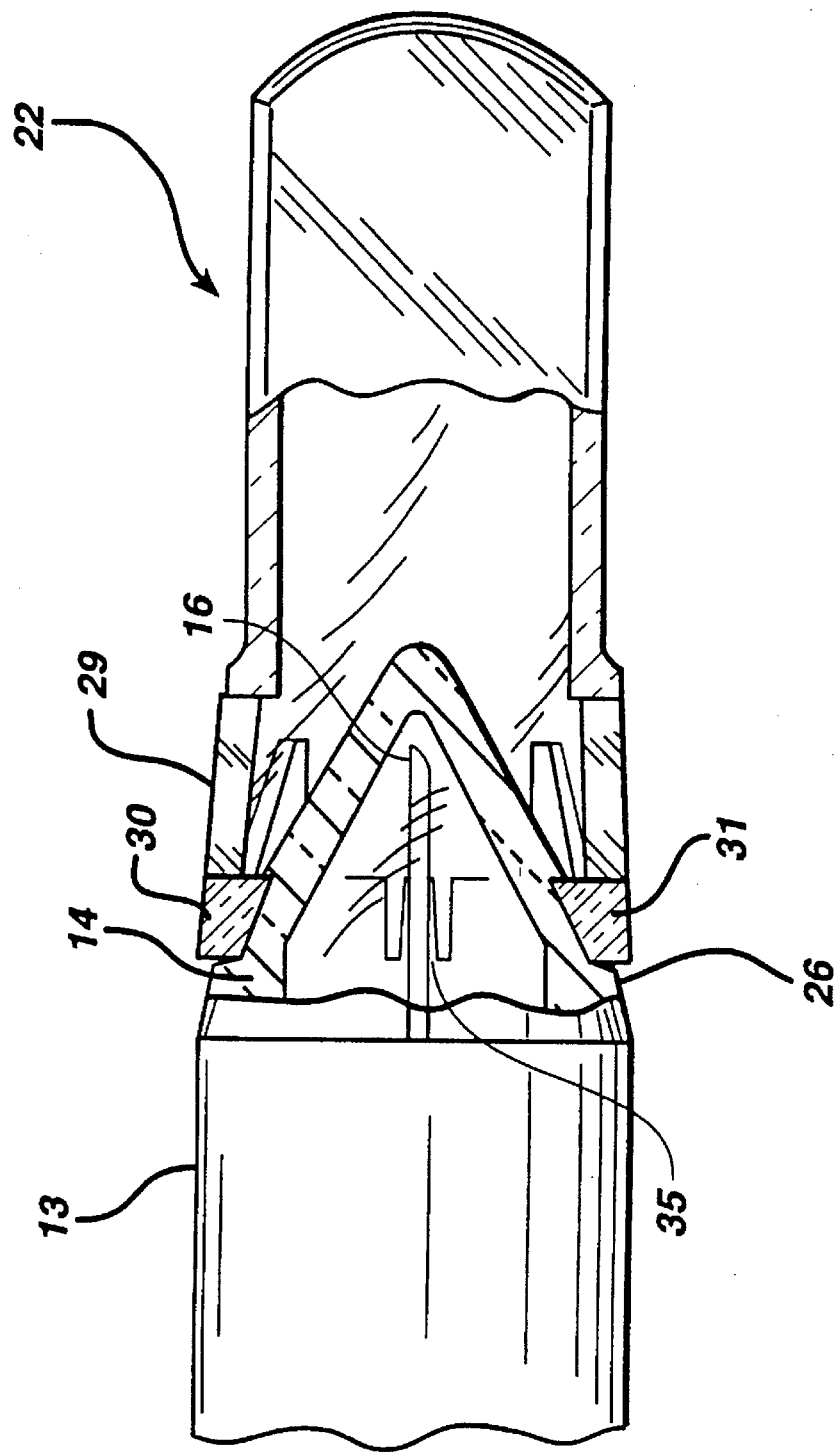
FIG. 9 is a partial cross-sectional view of the penetrating tip taken along line 9—9 of FIG. 8 shown with the protective cap in place.

The transparent penetrating tip 14 of the surgical penetration instrument 11 is covered with a protective cap 22, and will be described in more detail in connection with FIG. 8.

The assembly illustrated in FIG. 1, and in particular the surgical penetration instrument 11 of this invention, can be used to penetrate or dissect tissue while providing simultaneous visualization as the tissue is penetrated or dissected. As illustrated in FIG. 3, the assembly 10 is advanced in the direction illustrated by the arrow through bodily tissue 24 of a surgical patient 25. A conventional endoscope 23 can be inserted through the hollow shaft 12 of instrument 11 so that the endoscope is positioned adjacent the proximal end of transparent penetrating tip 14. The endoscope 23 is connected to a light source 34 to provide illumination through the transparent penetrating tip 14 to the surgical site. It is also connected to a video monitor 35 to display the illuminated images transmitted from the surgical site. In this way, the user can readily monitor the advance of instrument 11 through bodily tissue 24 from video monitor 35.

When the advancement of the surgical penetration instrument 11 is completed, the instrument and the endoscope 23 may be removed from cannula 17 of assembly 10, so that additional instrumentation can then be inserted through the cannula to the surgical site to complete a desired surgical procedure.

Referring now to FIGS. 2 and 5–8, the transparent, conical penetrating tip 14 of the surgical penetration instrument has a circular base 26 and a blunt point 34 extending distally from the base. The circular base 26 is positioned adjacent the shaft distal end 13. The first and second blades 15 and 16, respectively, have generally straight, linear edge surfaces 27 and 28, respectively. Each of the first and second blades 15 and 16 extend longitudinally from adjacent the circular base 26 toward point 34 of penetrating tip 14. The first and second blades are spaced about 180° from each other, and are positioned proximally of the point.

Figure 5:
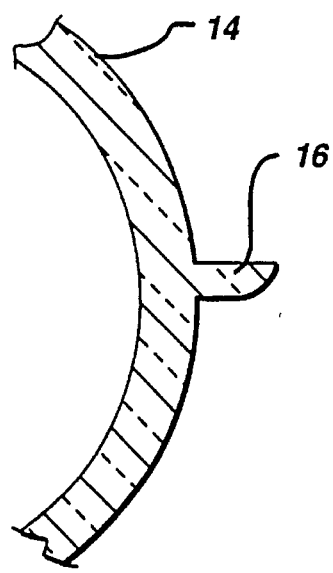
FIG. 5 is an enlarged fragmentary cross-sectional view taken through the blade which is formed integrally with the penetrating tip of the instrument as taken along section line 5—5 of FIG. 2.
Figure 6:
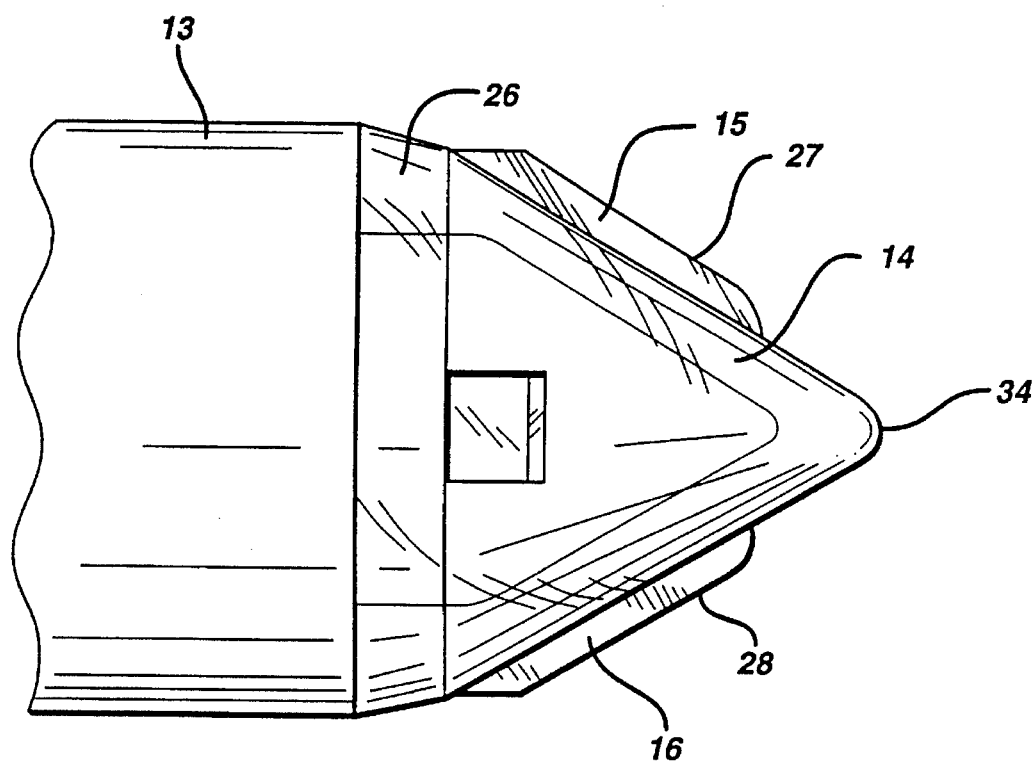
FIG. 6 is an enlarged top plan view of the penetrating tip of the instrument.
Figure 7:
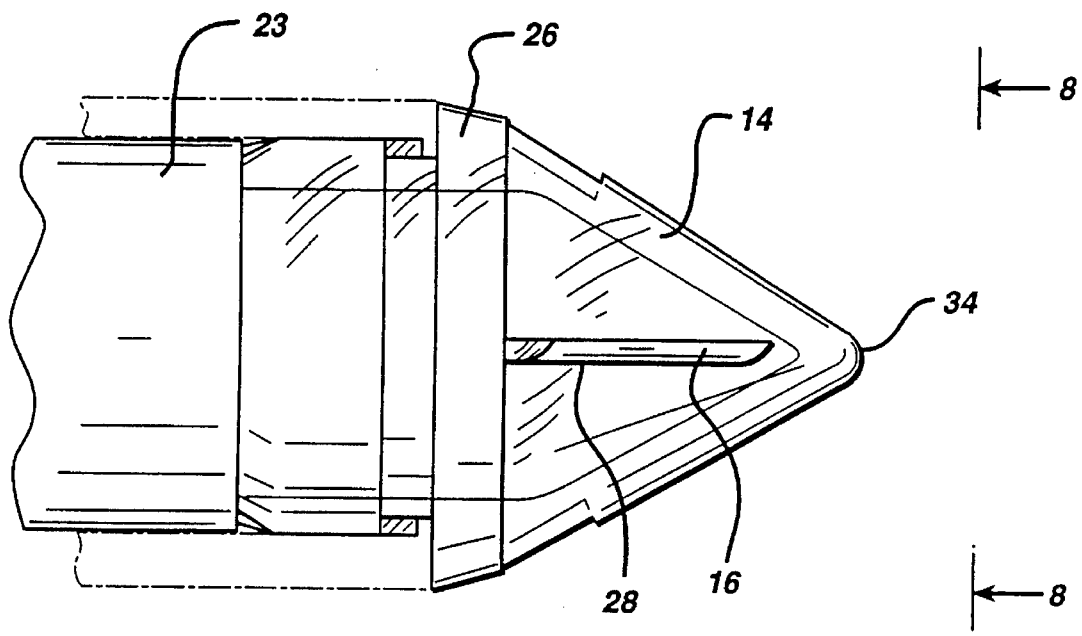
FIG. 7 is a side elevational view of the penetrating tip.

As best illustrated in FIG. 5, the blades extend integrally from the penetrating tip. In other words, the penetrating tip 14, and first and second blades 15 and 16 extending outwardly from it, are desirably constructed from a single piece of material. For example, the tip and blades may be manufactured using conventional plastic processing methods to form a single plastic piece. Alternatively, the tip and blades may be milled from a single piece of glass. In either case, the entire piece, including first and second blades 15 and 16, is transparent.

Preferably, penetrating tip 14 and first and second blades 15 and 16 are molded from a single piece of plastic. This plastic preferably exhibits a light transmission greater than about 75 percent, and a haze factor less than about 5 percent, in accordance with ASTM Standard D1003. The preferred plastic is a thermoplastic or thermoset polymer or ionomer. Examples of suitable polymers include, but are not limited to, acrylics, polycarbonates, polyesters and co-polyesters, polymethylpentene, polypropylene, polysulfones, cellulose acetate, styrene acrylic co-polymers, fluoropolymers, polystyrene, polyetherimides, styrene acrylonitrile, silicones, epoxys, polyvinyl chloride, urethanes, acrylonitrile-butadienestyrene (ABS), allyl diglycolcarbonate, as well as combinations or blends of these polymers. The preferred plastics are polyesters and coopolyesters, and the most preferred plastics are the co-polyesters.

Referring to FIGS. 1, 2, 8 and 9, the details of the protective cap 22 enclosing the penetrating tip 14 and the first and second blades 15 and 16, are illustrated. Protective cap 22 has a generally cylindrical sleeve portion 29 having a sleeve diameter sufficient to encircle the penetrating tip 14 and first and second blades 15 and 16 adjacent circular base 26 of the penetrating tip. In this way, the sleeve substantially encloses the plastic penetrating tip, including the blades, and shields these components during routine handling and care from breakage. The penetrating tip 14 has first and second square-shaped notches 32 and 33 displayed about 180° from each other adjacent circular base 26. The protective cap 22 correspondingly displays first and second tabs 30 and 31, respectively. These tabs engage the first and second notches 32 and 33 on penetrating tip 14 so that the protective cap 22 is securely fastened to the penetrating tip 14. Cylindrical sleeve portion 29 has a narrow slot 35 displayed at its proximal end. When the sleeve is attached to the penetrating tip, a portion of second blade 16 fills the slot. This prevents that portion of the blade from contacting the inner wall of the sleeve portion, and therefore prevents the blade from dulling. Similarly, a corresponding slot is displayed 180° from slot 35, and a portion of first blade 15 fills this slot (not shown in the drawings).

The reader should realize that this detailed description of the most preferred embodiment of the surgical penetration instrument of this invention does not preclude numerous additional embodiments which are not particularly illustrated in the drawings from falling within the scope of the appended claims. In other words, it is the appended claims which define the scope of the invention, and not this detailed description. One skilled in the art can readily envision numerous additional embodiments which fall within the scope of the appended claims. For example, the claimed invention should in no way be construed to be limited to a surgical penetration instrument having a penetrating tip with only two straight blades. More than two blades can extend from the penetrating tip, or for that matter, only one blade may extend from the tip and still be within the scope of the claimed invention. Similarly, the blade or blades need not be straight, but rather the blades may be helical in form, or some other configuration.

What is claimed is:

1. A surgical penetration instrument for penetrating bodily tissue during a surgical procedure; said instrument comprising an elongated shaft having a distal end; a penetrating tip in communication with said shaft distal end and extending distally therefrom, said penetrating tip having a surface configuration shaped to enlarge an opening in said bodily tissue as said instrument is advanced distally into said tissue; and a first transparent blade extending outwardly from said penetrating tip, wherein said penetrating tip and said first transparent blade are integrally formed from a single piece of material.

2. The instrument of claim 1 wherein said shaft is generally cylindrical and has a shaft diameter.

3. The instrument of claim 2 wherein said penetrating tip has a circular base and a base diameter, said circular base being adjacent said shaft distal end and having a base diameter substantially the same as said shaft diameter.

4. The instrument of claim 3 wherein said blade is composed of a transparent plastic or a glass.

5. The instrument of claim 4 wherein said blade is composed of a transparent plastic.

6. The instrument of claim 5 wherein said penetrating tip is composed of said plastic.

7. The instrument of claim 6 wherein said plastic exhibits a light transmission greater than about seventy five percent, and a haze factor less than about five percent.

8. The instrument of claim 7 wherein said plastic is a thermoplastic or thermoset polymer or ionomer.

9. The instrument of claim 8 wherein said said plastic is a copolyester.

10. The instrument of claim 5 wherein at least a portion of said penetrating tip is transparent.

11. The instrument of claim 10 wherein said transparent portion of said penetrating tip extends through substantially 360°.

12. The instrument of claim 11 wherein said instrument further comprises a second transparent blade extending outwardly from said penetrating tip.

13. The instrument of claim 12 wherein said penetrating tip is entirely transparent.

14. The instrument of claim 13 wherein said penetrating tip extends distally from said circular base to a point.

15. The instrument of claim 14 wherein said penetrating tip is generally conical.

16. The instrument of claim 15 wherein said first and second blades have straight linear edge surfaces.

17. The instrument of claim 16 wherein said first and second blades extend longitudinally from adjacent said circular base toward said point of said penetrating tip.

18. The instrument of claim 17 wherein said first and second blades are spaced about 180° from each other.

19. A surgical penetration instrument for penetrating bodily tissue during a surgical procedure; said instrument comprising a generally cylindrical, elongated shaft having a distal end and a shaft diameter; a plastic penetrating tip connected to said shaft distal end, said tip having a generally circular base adjacent said shaft distal end, said base having a base diameter substantially the same as said shaft diameter, said tip extending distally from said base and having an exterior surface configuration shaped to enlarge an opening in said bodily tissue as said instrument is advanced distally into said tissue; a protective cap sized to fit over and enclose at least a portion of said tip; cap receiving means on said exterior surface of said tip for securely receiving said cap; and cap attaching means on said cap for attaching said cap onto said cap receiving means.

20. The instrument of claim 19 wherein said cap has a generally cylindrical sleeve portion having a sleeve diameter, said sleeve diameter being substantially the same as said base diameter of said tip.

21. The instrument of claim 20 wherein said instrument further comprises a blade extending radially outwardly from said tip.

22. The instrument of claim 21 wherein said protective cap has a sleeve diameter sized to fit over and enclose a portion of said blade.

23. The instrument of claim 22 wherein said cap receiving means are first and second notches displayed on said exterior surface of said tip adjacent said circular base, said notches spaced about 180° from each other.

24. The instrument of claim 23 wherein said cap attaching means are first and second tabs displayed on said sleeve, said first and second tabs engagable with said first and second notches.

* * * * *